United States Patent [19]
Higuchi

[11] Patent Number: 5,994,056
[45] Date of Patent: Nov. 30, 1999

[54] HOMOGENEOUS METHODS FOR NUCLEIC ACID AMPLIFICATION AND DETECTION

[75] Inventor: Russell G. Higuchi, San Francisco, Calif.

[73] Assignee: Roche Molecular Systems, Inc., Pleasanton, Calif.

[21] Appl. No.: 07/695,201

[22] Filed: May 2, 1991

[51] Int. Cl.$^6$ .............................. C12P 1/48; C12P 1/68; C12N 15/10

[52] U.S. Cl. .............................. 435/6; 435/91.2; 435/810; 436/63; 436/94

[58] Field of Search ................................. 435/6, 91, 810, 435/91.2; 436/63, 94; 935/17, 77, 78

[56] References Cited

U.S. PATENT DOCUMENTS

| | | | |
|---|---|---|---|
| 4,119,521 | 10/1978 | Chirikjian | 204/299 |
| 4,257,774 | 3/1981 | Richardson et al. | 23/230 |
| 4,582,789 | 4/1986 | Sheldon, III et al. | 435/6 |
| 4,683,195 | 7/1987 | Mullis et al. | 435/6 |
| 4,683,202 | 7/1987 | Mullis | 435/91 |
| 4,889,818 | 12/1989 | Gelfand et al. | 435/194 |
| 5,049,490 | 9/1991 | Sutherland et al. | 435/6 |

FOREIGN PATENT DOCUMENTS

| | | |
|---|---|---|
| 0070685 | 1/1983 | European Pat. Off. |
| 0487218 | 5/1992 | European Pat. Off. |
| 9015881 | 12/1990 | WIPO |

OTHER PUBLICATIONS

Kirk–Othmer, "Antibiotics (Phenazines) to Bleaching Agents," *Encyclopedia of Chemical Technology (Third Edition)*, 3:906–907.

Byrnes, J.J., et al., "Bone Marrow Cytoplasmic Deoxyribonucleic Acid polymerase, Variation of pH and Ionic Environment as a Possible Control Mechanism," *Biochemistry*, 12/22:4378–4384 (1973).

Lomell, H., et al., "Quantitative Assays Based on the use of Replicatable Hybridization Probes," *Clin. Chem.*, 35/9:1826–1831 (1989).

Isaacs et al., Jan., 1991, "Post–PCR Sterilization: Development and Application to an HIV–1 Diagnostic Assay" Nucleic Acids Research 19(1):109–116 (1991).

Share et al., 1973, Biochemistry 12:3055.

Morrison et al., 1989, Anal. Biochem. 183:231–244.

Glazer et al., 1990. Proc. Natl. Acad. Sci. USA 87:3851–3855.

Mabuchi and Nishikawa, 1990, Nuc. Acids Res. 18(24):7461–7462.

Oser and Valet, 1990, Angew. Chem. Int. Engl. 29(10):1167.

Sobel and Jair 1972, J. Mol. Biol. 68:21–34.

Kapuseinski and Szer, 1979, Nuc. Acids Res. 6(112):3519–3535.

Johnson and Hearst, 1981, Photochem. and Photobiol. 33:785–791.

Khattar et al., 1990, JACS 112:4960.

Searle and Embrey, 1990, Nuc. Acids Res. 18(13):3653–3762.

Richardson, 1973, J. Mol. Biol. 78:703–714.

Kornberg, 1974, in DNA Synthesis, W.H. Freman and Co., San Francisco, pp. 220–236.

*Primary Examiner*—Robert A. Wax
*Assistant Examiner*—Rebecca Prouty
*Attorney, Agent, or Firm*—Douglas A. Petry

[57] ABSTRACT

This invention relates to improved methods for nucleic acid detection using methods such as the polymerase chain reaction (PCR). More specifically, the invention provides methods for simultaneous amplification and detection to enhance the speed and accuracy of prior methods. The methods involve the introduction of detectable DNA binding agents into the amplification reaction, which agents produce a detectable signal that is enhanced upon binding double-stranded DNA. In a preferred embodiment, the binding agent is a fluorescent dye. The methods also provide means for monitoring the increase in product DNA during an amplification reaction.

21 Claims, 6 Drawing Sheets

Homozygous AA

Heterozygous AS

Homozygous SS

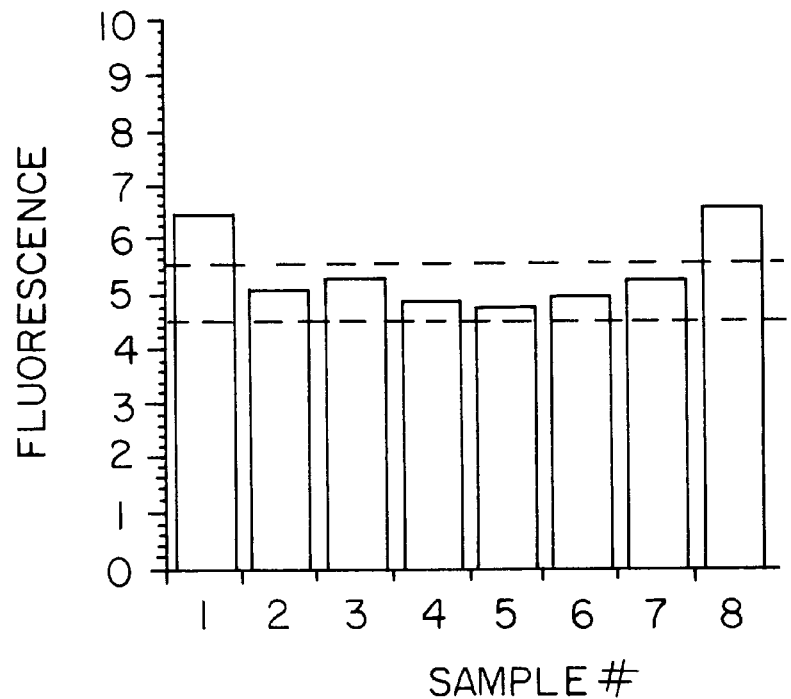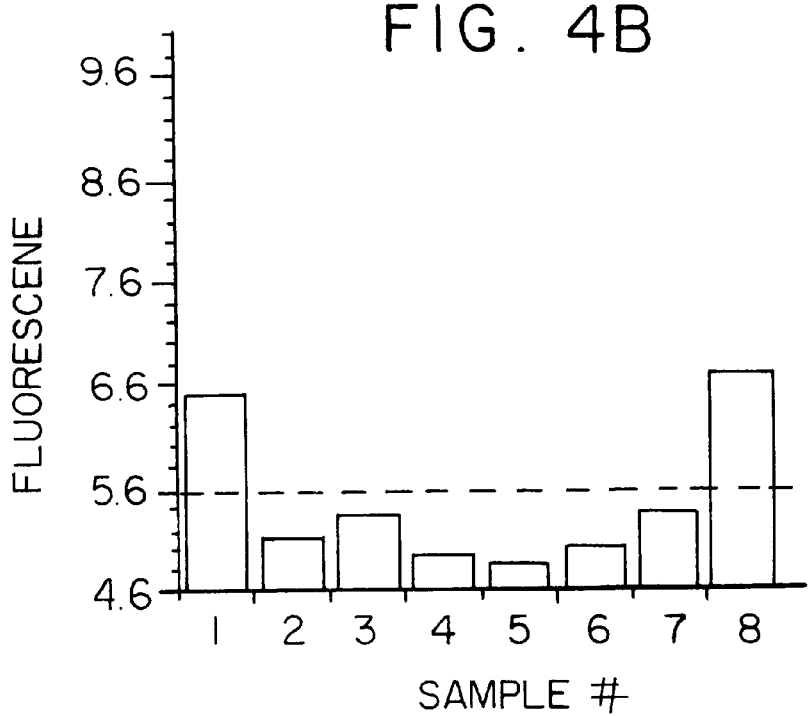

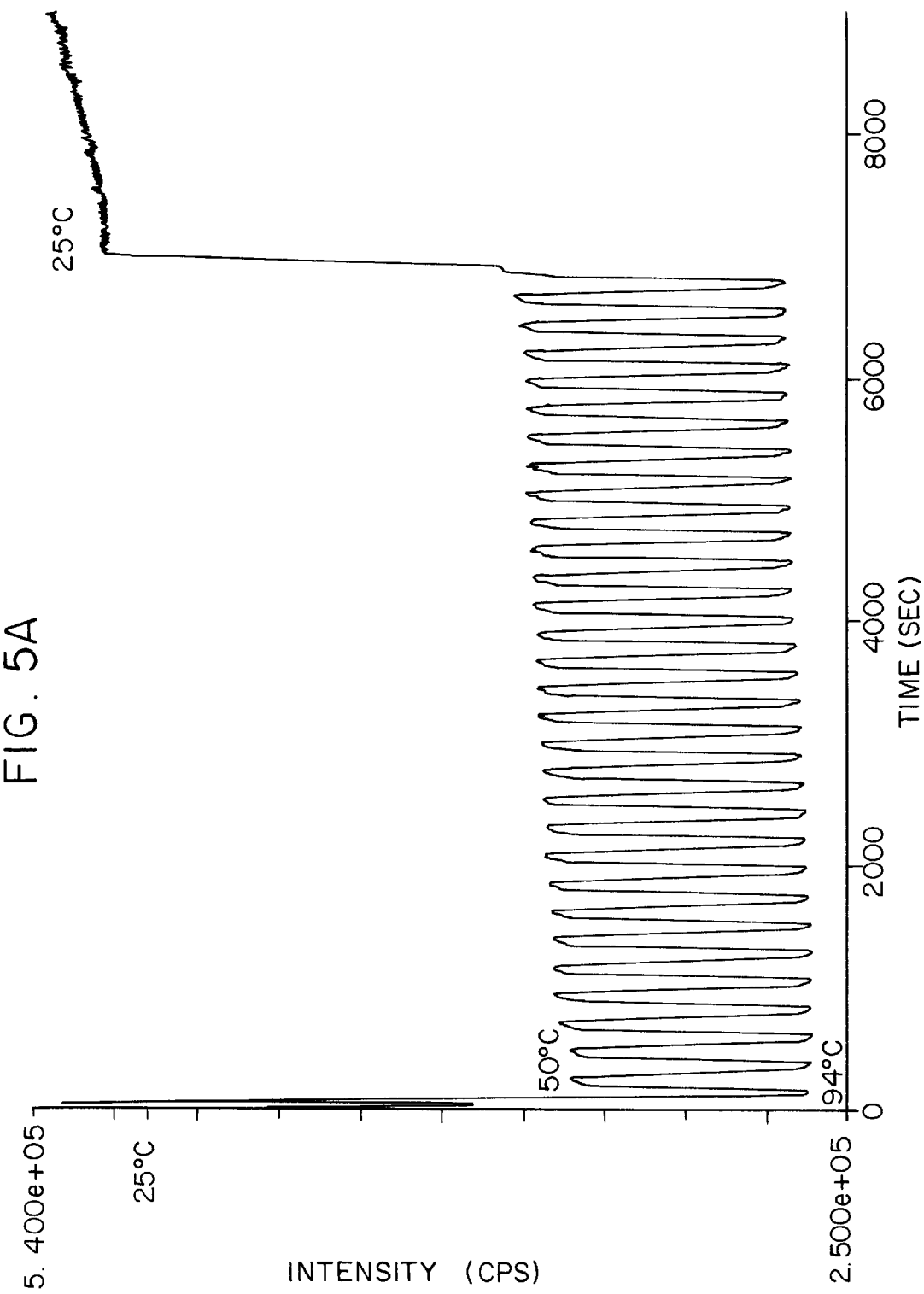

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 26 base pairs

```
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:1:

GTGCTGCAGG TGTAAACTTG TACCAG                                           26

(2) INFORMATION FOR SEQ ID NO:2:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:2:

CACGGATCCG GTAGCAGCGG TAGAGTTG                                         28

(2) INFORMATION FOR SEQ ID NO:3:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:3:

GTGTAAACTT GTACCAG                                                     17

(2) INFORMATION FOR SEQ ID NO:4:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:4:

GGTAGCAGCG GTAGAG                                                      16

(2) INFORMATION FOR SEQ ID NO:5:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

CCGGATCCTT CGTGTCCCCA CAGCACG                                          27

(2) INFORMATION FOR SEQ ID NO:6:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)
```

(xi) SEQUENCE DESCRIPTION: SEQ ID NO:6:

CTCCCCAACC CCGTAGTTGT GTCTGCA                                27

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TCCACTTTAT TCCAGGCCTG T                                      21

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

TTGAATGGAA TGGGAACGAA TGG                                    23

(2) INFORMATION FOR SEQ ID NO:9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

AATAGACCAA TAGGCAGAG                                         19

(2) INFORMATION FOR SEQ ID NO:10:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CACCTGACTC CTGA                                              14

(2) INFORMATION FOR SEQ ID NO:11:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CACCTGACTC CTGT                                              14

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CCAGGCCAGA TGAGAGAACC AAGGGG                                            26

(2) INFORMATION FOR SEQ ID NO:13:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GCGGGCAGGG CGGCGGGGGC GGGGCCGAAC CGGTCTACAT AGTCTCTAAA GGG        53

(2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GGTCCCTGTC TTATGTC                                                                17

HOMOGENEOUS METHODS FOR NUCLEIC ACID AMPLIFICATION AND DETECTION

BACKGROUND OF THE INVENTION

1. Field of the Invention

The present invention provides improved methods for nucleic acid detection. The novel methods for simultaneous nucleic acid amplification and detection enhance the speed and accuracy of prior detection methods and eliminate the need for sample processing following amplification. In a preferred embodiment, the method provides a modification of the polymerase chain reaction and utilizes agents whose fluorescence is enhanced upon binding double-stranded DNA. The methods provided herein have numerous applications, particularly in the fields of molecular biology, medical diagnostics and forensic sciences.

2. Description of Related Art

The disclosed nucleic acid detection methods offer the advantages of speed and simplicity over prior methods for detecting amplified nucleic acids. Nucleic acid detection techniques in general are particularly useful in medical diagnostic assays. For example, Falkow et al., U.S. Pat. No. 4,358,535 disclose a method for detecting pathogens by spotting a sample (e.g., blood, cells, saliva, etc.) on a filter, lysing the cells and fixing the DNA through chemical denaturation and heating. Then, labeled DNA probes are added and allowed to hybridize with the fixed sample DNA. Hybridization indicates the presence of the pathogen's DNA.

Nucleic acid detection using oligonucleotide probes has become a standard method for specific target detection. Numerous modifications of the method have been described, including culturing the target cells or organisms in situ on the filter, increasing the amount of target nucleic acid available for detection. Generally, these methods require that the DNA sample is noncovalently bound onto a solid support such as nitrocellulose or nylon and then hybridized to a labeled target-specific probe.

The sensitivity and specificity of nucleic acid detection methods was greatly improved by the invention of the polymerase chain reaction (PCR). PCR is a process for amplifying nucleic acids and involves the use of two oligonucleotide primers, an agent for polymerization, a target nucleic acid template, and successive cycles of denaturation of nucleic acid and annealing and extension of the primers to produce a large number of copies of a particular nucleic acid segment. With this method, segments of single copy genomic DNA can be amplified more than 10 million fold with very high specificity and fidelity. PCR methods are disclosed in U.S. Pat. No. 4,683,202, which is incorporated herein by reference.

Methods for detecting PCR products are particularly described in U.S. Pat. No. 4,683,195, which is incorporated herein by reference. Those methods require an oligonucleotide probe capable of hybridizing with the amplified target nucleic acid. European Patent Publication No. 237,362, which is incorporated herein by reference, also describes a PCR-based detection method termed "reverse dot blot", in which the probe, instead of the amplified DNA, is fixed to the membrane. According to the method, the target, rather than the probe, is labeled for hybridization. These methods require separate steps of amplification, capture, and detection and generally require several hours to complete. In the reverse dot-blot method, storage-stable target-specific reagents are preferred.

Alternative methods for detecting amplified nucleic acids are described in copending U.S. Ser. No. 076,394, filed Jul. 22, 1987, which is incorporated herein by reference. U.S. Ser. No. 076,394 describes PCR-based methods for simultaneous amplification and labeling of a target nucleic acid. The methods require that at least one amplification primer is labeled. The amplification primer can be labeled with, for example, a radioisotope for direct detection of the amplified product or labeled with a reagent suitable for capturing the product onto a solid support for subsequent detection.

Other means of detection include the use of fragment length polymorphism hybridization, allele-specific oligonucleotide (ASO) probes (Saiki et al., 1986, *Nature* 324:163), or direct sequencing via the dideoxy method using amplified DNA rather than cloned DNA. The fragment length polymorphism method detects insertions and deletions between PCR primers resulting in PCR products of different lengths, detectable by sizing. ASO methods are useful for detecting allelic sequence variations. In an example of ASO hybridization, the amplified DNA is fixed to a nylon filter (by, for example, UV irradiation) in a series of "dot blots," then allowed to hybridize with an oligonucleotide probe under stringent conditions. This method is also described in copending U.S. Ser. No. 347,495, filed May 4, 1989, which is incorporated herein by reference. The probe may be labeled with, for example, horseradish peroxidase (HRP) and detected by the presence of a blue precipitate following treatment with suitable oxidation reagents.

Copending U.S. Ser. No. 563,758, filed Aug. 6, 1990, and incorporated herein by reference, describes an alterative assay method for detecting amplified nucleic acids. The process employs the 5' to 3' nuclease activity of a nucleic acid polymerase to cleave annealed, labeled oligonucleotides from hybridized duplexes and release labeled oligonucleotide fragments for detection. The method is suitable for detecting PCR products and requires a primer pair and a labeled oligonucleotide probe having a blocked 3'-0H terminus to prevent extension by the polymerase.

Due to the enormous amplification possible with the PCR process, small levels of DNA carryover from samples with high DNA levels, positive control templates, or from previous amplifications, can result in PCR product even in the absence of purposefully added template DNA. Higuchi and Kwok, (1989, *Nature* 339:237–238 and Kwok) and Orrego, (in Innis et al., 1990, *PCR Protocols: A Guide to Methods and Applications*, Academic Press, Inc., San Diego, Calif.), describe particular methods and precautions for practicing PCR with a minimum of cross contamination. U.S. Ser. No. 609,157, filed Nov. 2, 1990, describes improved methods for reducing the effects of cross contamination by the introduction of unconventional nucleotide bases. These references are incorporated herein by reference. Because the possibility of introducing contaminating DNA to a sample will be increased as the amount of handling steps required for sample preparation, processing, and analysis is increased, it would be preferable to minimize sample handling, particularly after the amplification reaction is complete.

A number of agents have been described for labeling nucleic acids, whether probe or target, for facilitating detection of target nucleic acid. Suitable labels may provide signals detectable by fluorescence, radioactivity, colorimetry, X-ray diffraction or absorption, magnetism or enzymatic activity and include, for example, fluorophores, chromophores, radioactive isotopes (particularly $^{32}$P and $^{125}$I) electron-dense reagents, enzymes, and ligands having specific binding partners.

Labeling is achieved by a number of means, such as chemical modification of a primer or probe to incorporate a label or the use of polymerizing agents to incorporate a modified nucleoside triphosphate into an extension product. Intercalating agents non-covalently bind the stacked bases of nucleic acids and as a result the fluorescence of the agent either increases or shifts to a different wavelength. For example, U.S. Pat. No. 4,582,789 describes several intercalating moieties including psoralens. Copending U.S. Ser. No. 076,394 describes methods for amplifying and detecting nucleic acids using psoralen labeled primers. Both the '789 patent and the '394 application are incorporated herein by reference.

Fluorescent dyes are suitable for detecting nucleic acids. For example, ethidium bromide is an intercalating agent that displays increased fluorescence when bound to double-stranded DNA rather than when in free solution (Sharp et al., 1973, *Biochemistry* 12:3055). Ethidium bromide can be used to detect both single- and double-stranded nucleic acids, although the affinity of ethidium bromide for single-stranded nucleic acid is relatively low. Ethidium bromide is routinely used to detect nucleic acids following gel electrophoresis. Following size fractionation on an appropriate gel matrix, for example, agarose or acrylamide, the gel is soaked in a dilute solution of ethidium bromide. The DNA is then visualized by examining the gel under UV light (see Maniatis et al., 1982 eds., *Molecular Cloning: A Laboratory Manual*, New York, Cold Spring Harbor Laboratory.)

Alternative fluorescence based methods for detecting DNA have been described. For example, Morrison et al., 1989, *Anal. Biochem.*, 18:231–244, which is incorporated herein by reference, describe a two probe method for detecting target DNA. One probe is labeled with fluorescein, the other probe, complementary to the first, is labeled with a quencher for fluorescein emission. The probes are allowed to anneal with denatured DNA containing the target sequence, and the amount of fluorescence is determined. Fluorescence increases to the extent that the fluorescein probe binds to unlabeled, complementary DNA rather than the complementary, quenching probe.

Mabuchi et al., 1990, *Nucl. Acids Res.* 18(24):7461–7462, which is incorporated herein by reference, describe a method for detecting DNA fragments based on the AT content of the nucleic acid segment. Two fluorochromes are used to stain size fractionated DNA in an agarose gel. The selective binding properties of different fluorochromes for AT rich regions are used to distinguish electrophoresed DNA fragments.

U.S. Pat. No. 4,257,774, which is incorporated herein by reference, describes the direct binding of fluorescent intercalators to DNA, e.g., ethidium salts, daunomycin, mepacrine and acridine orange, as well as 4'6-diamidino-α-phenylindole to quantitate the DNA. Fluorescence polarization is used for characterization of non-fluorescent DNA binding compounds which compete with the DNA binding dyes.

Oser and Valet (1990, *Angew. Chem. Int. Engl.* 29(10):1167) describe a nucleic acid detection scheme that requires two oligonucleotide probes complementary to adjacent sites on a target. The probes are labeled differentially with either a salicylate or a DTPA ligand bearing a fluorescence emitter, $Tb^{III}$. Hybridization of both probes to the target provides steric proximity of the two labels resulting in a measurable increase in $Tb^{III}$ fluorescence. The modified probes are prepared specifically for each target to be detected.

European Patent Publication No. 070,685 describes the use of fluorescent labeled polynucleotide probes in polynucleotide hybridization assays. According to the method, probes are prepared by attaching particular absorber-emitter moieties to the 3' and 5' ends of nucleic acid fragments. The fragments are capable of hybridizing to adjacent positions on a target DNA, so that, if both fragments are hybridized, the proximity of the absorber and emitter moieties results in detectable emitter fluorescence.

According to these methods, the fluorescent dye is introduced to the target DNA after all in vitro nucleic acid polymerization reactions have been completed. The inhibitory effects of intercalating agents on nucleic acid polymerases have been described in numerous publications (see for example, Kornberg, 1974, *DNA Synthesis*, W. H. Freman and Co., San Francisco, and Richardson, 1973, *J. Mol. Biol.* 78:703–714, which is incorporated herein by reference).

DNA binding dyes are useful as antibiotics because of the inhibitory effects on nucleic acid replication processes that result from the agent binding to the template. European Patent Publication No. 169,787 describes the use of intercalating agents for blocking replication of influenza or herpes virus. Kornberg (supra) describes a number of DNA binding agents, both intercalators and non-intercalators, and describes how each compound inhibits nucleic acid replication. At page 227, Kornberg specifically describes that ethidium bromide inhibits DNA replication.

A method for simultaneous amplification and detection of target nucleic acids would provide advantages over prior detection methods. Such a method would minimize the problems of sample contamination inherent in any process involving a series of manipulative steps for discerning a positive or negative test result. By eliminating sample handling and processing steps, a method for simultaneous amplification and detection of target nucleic acids would increase the speed and accuracy of current diagnostic methods. The present invention addresses and solves these needs.

SUMMARY OF THE INVENTION

The present invention provides a method for detecting a target nucleic acid in a sample. The method comprises the steps of: (a) providing an amplification reaction mixture that comprises a sample, a DNA binding agent, wherein said agent is characterized as providing a detectable signal when bound to double-stranded nucleic acid which signal is distinguishable from the signal provided by said agent when it is unbound, and reagents for amplification; (b) determining the amount of signal produced by the mixture of step (a); (c) treating said mixture under conditions for amplifying the target nucleic acid; (d) determining the amount of said signal produced by the mixture of step (c); and (e) determining if amplification has occurred.

The invention is particularly suitable for practice in PCR amplification methods wherein a net increase in double-stranded DNA results in a change in signal strength or type. In a preferred embodiment, the DNA binding agent is a fluorescent DNA binding dye, such as ethidium bromide, and the signal is fluorescence.

BRIEF DESCRIPTION OF THE DRAWINGS

FIGS. 4A and 4B relate to the quantitative homogeneous assay described in Example VII. FIG. 4A demonstrates that the increase in fluorescence in the positive samples is greater than two standard deviations away from the average of the negative samples. FIG. 4B graphically describes a background substraction method for measuring fluorescence.

FIGS. 5A and 5B demonstrate the results of an on-line, automated homogeneous amplification and detection system, according to the present invention as demonstrated in Example VIII. FIG. 5A shows a fluorescence print-out from a PCR containing no target DNA and serves as a negative control. FIG. 5B is a fluorescence print out from a PCR containing the appropriate target and demonstrates the continuous monitoring of the PCR and concurrent increase in PCR product.

DETAILED DESCRIPTION

Figure 1:
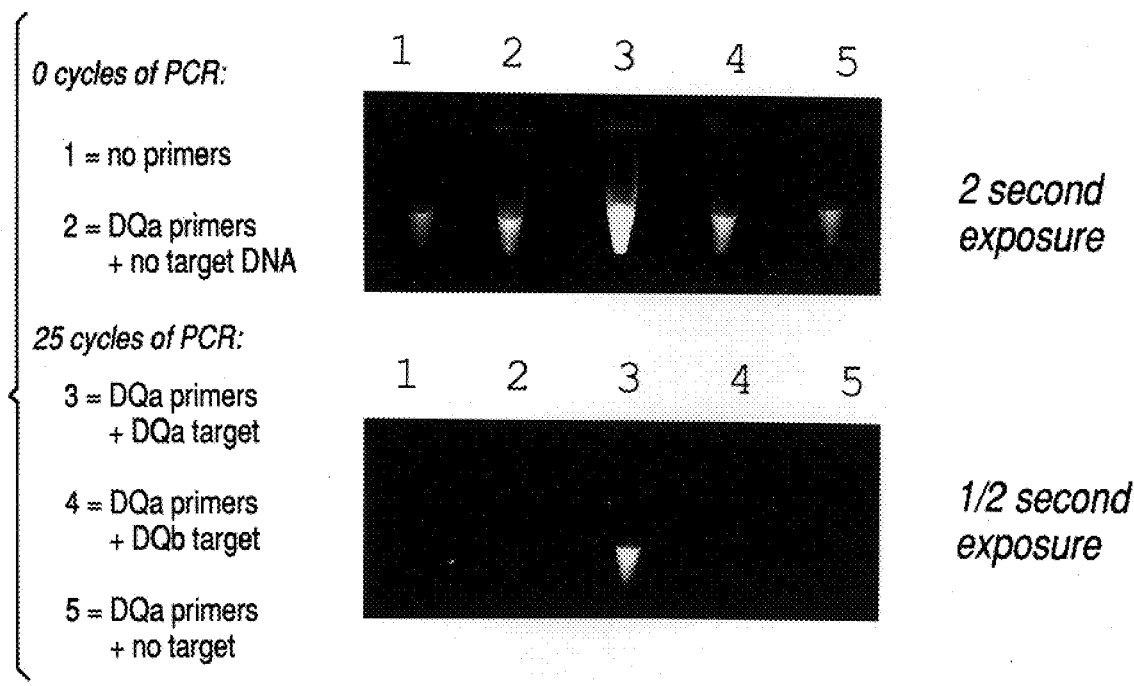
FIG. 1 demonstrates the increased fluorescence of the PCR mixture due to amplification of a specific target DNA in the presence of ethidium bromide. The experiment is described in detail in Example II.

The present invention provides improved methods for detecting nucleic acids and is especially suited for use in conjunction with amplification processes. The improved methods require neither an oligonucleotide probe nor a labeled amplification primer. The methods enable monitoring the accumulation of product while the amplification reaction is in progress. The invention also allows target specific quantitation. These methods are suitable for use in automated formats.

The methods disclosed offer vast improvements over prior methods for detecting amplified nucleic acids. According to the invention, amplified nucleic acids are detected without opening the reaction vessel once the amplification reaction is initiated and without any additional handling or manipulative steps subsequent to the reaction. Prior to the present invention, nucleic acid detection methods required a third oligonucleotide reagent as a probe, or a series of manipulative and time consuming steps for target detection, for example, capturing the product on a solid support, which steps are performed after amplification. In some procedures both capture and probe hybridization steps are required. The present invention eliminates the need for using a hybridizing probe reagent or a capture procedure for detecting the amplified target. In a clinical setting the methods of the invention offer speed, simplicity, and decreased opportunity for cross-contamination between samples, particularly between amplified and non-amplified samples. In addition, the present methods offer means for automated detection, monitoring and quantitation of amplification products during the amplification process and after the amplification reaction is complete.

The present methods require a detectable agent capable of binding double-stranded DNA. The detectable binding agent may be a fluorescent dye or other chromophore, enzyme, or agent capable of producing a signal, directly or indirectly, when bound to double-stranded DNA. The agent may be also characterized as binding to single-stranded DNA or RNA. It is only necessary that the agent is capable of producing a detectable signal when bound to a double-stranded nucleic acid that is distinguishable from the signal produced when that same agent is in solution or bound to a single-stranded nucleic acid.

In one embodiment, the DNA binding agent is an intercalating agent. As used herein, an intercalating agent is an agent or moiety capable of non-covalent insertion between stacked base pairs in the nucleic acid double helix. Intercalating agents, such as ethidium bromide, fluoresce more intensely when intercalated into double-stranded DNA than when bound to single-stranded DNA, RNA, or in solution. Other intercalating agents exhibit a change in the fluorescence spectra when bound to double-stranded DNA. For example, actinomycin D fluoresces red when bound to single-stranded nucleic acids, and green when bound to a double-stranded template. Whether the detectable signal increases, decreases or is shifted, as is the case with actinomycin D, any intercalating agent that provides a detectable signal that is distinguishable when the agent is bound to double-stranded DNA or unbound is suitable for practicing the disclosed invention. For example, the interaction between DNA and another photoreactive psoralen, 4-aminomethyle-4-5'8-trimethylpsoralen (AMT) has been described (see Johnson et al. 1981, *Photochem. & Photobiol.*, 33:785–791, which is incorporated herein by reference). According to the reference, both the absorption at long wavelengths and fluorescence, decline upon intercalation of AMT into the DNA helix.

Non-intercalating DNA binding agents are also suitable. For example, Hoechst 33258 (Searle & Embrey, 1990, *Nuc. Acids Res.* 18(13):3753–3762) exhibits altered fluorescence with increasing amount of target. Hoechst 33258 is a member of a class of DNA-binding compounds commonly referred to as "groove binders." This group includes drugs like distamycin, netropsin and others. These compounds recognize and bind the minor groove of duplex DNA.

According to the present invention, a DNA binding agent produces a detectable signal directly or indirectly. The signal is detectable directly, such as by fluorescence or absorbance, or indirectly via a substituted label moiety or binding ligand attached to the DNA binding agent. For indirect detection any moiety or ligand that is detectably affected by proximity to double-stranded DNA is suitable.

According to the invention, the detectable binding agent is present in the amplification reaction during the amplification process. As amplification proceeds, the agent produces a detectable signal. Neither the agent nor the signal prevents amplification from proceeding. Consequently, the agent may be added to the reaction mixture prior to amplification or while the reaction is in progress. For example, the agent is included in an amplification buffer comprising appropriate reagents, such as salts and buffering agents. In this manner, it is not necessary to separately add the binding agent to the amplification reaction. For practice of the present invention, any DNA binding agent is suitable, so long as in the presence of that agent a net increase in the amount of double-stranded DNA present is reflected in a change signal intensity that is detectable directly or indirectly. In a preferred embodiment, the detectable signal is fluorescence.

The term "homogeneous detection assay" is used in the present specification to describe the claimed invention. For ease of understanding, the following definition is provided. Homogeneous detection assay refers to a method for coupled amplification and detection, wherein the process of amplification generates a detectable signal and the need for subsequent sample handling and manipulation to detect the amplified product is minimized or eliminated.

The present homogeneous assay is suitable for use in conjunction with oligonucleotide probes. For example, in one embodiment the use of an oligonucleotide probe, specific for detecting a particular target sequence, is included in the amplification reaction in addition to the DNA binding agent of the present invention. The probe, labeled with a quencher and fluorophore, hybridizes to the amplified target nucleic acid. In the presence of an agent for polymerization capable of 5' to 3' nucleolytic activity, the fluorophore and quencher, when bound to the target, are separated by degradation of the probe by the polymerase. The fluorescence of the unbound probe is detectably distinct from the fluorescence of the bound, and subsequently hydrolyzed probe. Thus, the fluorescence of the DNA binding agent enables detection that amplification has occurred, and the fluorescence of the hybridized probe indicates target specific amplification. So long as amplification is detectable without opening the reaction vessel, or further processing steps once amplification is initiated, the method is within the present definition of a homogeneous assay.

The term "amplification reaction system" refers to any in vitro means for multiplying the copies of a target sequence of nucleic acid. Such methods include but are not limited to polymerase (PCR), DNA ligase, (LCR), Qβ RNA replicase, and RNA transcription-based (TAS and 3SR) amplification systems.

The term "amplifying" which typically refers to an "exponential" increase in target nucleic acid is being used herein to describe both linear and exponential increases in the numbers of a select target sequence of nucleic acid.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Depending upon the context, the mixture can be either a complete or incomplete amplification reaction mixture.

The systems described below are practiced routinely by those of skill in the relevant art. They have been described in detail by others and are summarized below. This invention is not limited to any particular amplification system. As other systems are developed, those systems may benefit by practice of this invention. A recent survey of amplification systems was published in *Bio/Technology* 8:290–293, April 1990, incorporated herein by reference. The following four systems are described below for the convenience of those not familiar with amplification systems and to provide an understanding of the breadth of the present invention.

Amplification of DNA by PCR is disclosed in U.S. Pat. Nos. 4,683,195 and 4,683,202 (both of which are incorporated herein by reference). Methods for amplifying and detecting nucleic acids by PCR using a thermostable enzyme are disclosed in U.S. Pat. No. 4,965,188, which is incorporated herein by reference.

PCR amplification of DNA involves repeated cycles of heat-denaturing the DNA, annealing two oligonucleotide primers to sequences that flank the DNA segment to be amplified, and extending the annealed primers with DNA polymerase. The primers hybridize to opposite strands of the target sequence and are oriented so that DNA synthesis by the polymerase proceeds across the region between the primers, effectively doubling the amount of the DNA segment. Moreover, because the extension products are also complementary to and capable of binding primers, each successive cycle essentially doubles the amount of DNA synthesized in the previous cycle. This results in the exponential accumulation of the specific target fragment, at a rate of approximately 2 n per cycle, where n is the number of cycles.

In the disclosed embodiment, Taq DNA polymerase is preferred although this is not an essential aspect of the invention. Taq polymerase, a thermostable polymerase, is active at high temperatures. Methods for the preparation of Taq are disclosed in U.S. Pat. No. 4,889,818 and incorporated herein by reference. Taq polymerase is available from Perkin Elmer Cetus Instruments (PECI). However, other thermostable DNA polymerases isolated from other Thermus species or non Thermus species (e.g., *Thermus thermophilus* or *Thermotoga maritima*), as well as non-thermostable DNA polymerase such as T4 DNA polymerase, T7 DNA polymerase, *E. coli* DNA polymerase I, or the Klenow fragment of *E. coli*, can also be used in PCR. Methods for providing thermostable DNA polymerases are provided in copending Ser. Nos. 455,967, filed Dec. 22, 1989; 567,244, filed Aug. 13, 1990; and 590,213, 590,466, and 590,490, filed Sep. 28, 1990, which are all incorporated herein by reference.

As used herein, the term "primer" refers to an oligonucleotide capable of acting as a point of initiation of DNA synthesis when annealed to a nucleic acid template under conditions in which synthesis of a primer extension product is initiated, i.e., in the presence of four different nucleotide triphosphates and a DNA polymerase in an appropriate buffer ("buffer" includes pH, ionic strength, cofactors, etc.) and at a suitable temperature.

The nucleoside-5'-triphosphates utilized in the extension process, typically dATP, dCTP, dGTP, and dTTP, are present in total concentration typically ranging from 400 $\mu$M to 4.0 mM during the extension reaction, although preferably the concentration is between 500 $\mu$M and 1.5 mM.

The choice of primers for use in PCR determines the specificity of the amplification reaction. Primers used in the present invention are oligonucleotides, usually deoxyribonucleotides several nucleotides in length, that can be extended in a template-specific manner by the polymerase chain reaction. The primer is sufficiently long to prime the synthesis of extension products in the presence of the agent for polymerization and typically contains 10–30 nucleotides, although that exact number is not critical to the successful application of the method. Short primer molecules generally require cooler temperatures to form sufficiently stable hybrid complexes with the template.

Synthetic oligonucleotides can be prepared using the triester method of Matteucci et al., 1981, *J. Am. Chem. Soc.* 103:3185–3191. Alteratively automated synthesis may be preferred, for example, on a Biosearch 8700 DNA Synthesizer using cyanoethyl phosphoramidite chemistry.

For primer extension to occur, this primer must anneal to the nucleic acid template. Not every nucleotide of the primer must anneal to the template for extension to occur. The primer sequence need not reflect the exact sequence of template. For example, a non-complementary nucleotide fragment may be attached to the 5' end of the primer with the remainder of the primer sequence being complementary to the template. Alteratively, non-complementary bases can be interspersed into the primer, provided that the primer sequence has sufficient complementarily with the template for annealing to occur and allow synthesis of a complementary DNA strand.

Amplification systems such as PCR require a target nucleic acid in a buffer compatible with the enzymes used to amplify the target. The target nucleic acid can be isolated from a variety of biological materials including tissues, body fluids, feces, sputum, saliva, plant cells, bacterial cultures, and the like.

In general, the nucleic acid in the sample will be a sequence of DNA, most usually genomic DNA. However, the present invention can also be practiced with other nucleic acids, such as messenger RNA, ribosomal RNA, viral RNA, or cloned DNA. Suitable nucleic acid samples include single or double-stranded DNA or RNA for use in the present invention. Those of skill in the art will recognize that whatever the nature of the nucleic acid, the nucleic acid can be amplified merely by making appropriate and well recognized modifications to the method being used.

To amplify a target nucleic acid sequence in a sample, the sequence must be accessible to the components of the amplification system. In general, this accessibility is ensured by isolating the nucleic acids from a crude biological sample. A variety of techniques for extracting nucleic acids from biological samples are known in the art. For example, see those described in Maniatis et al., *Molecular Cloning: A Laboratory Manual* (New York, Cold Spring Harbor Laboratory, 1982); Arrand, Preparation of Nucleic Acid Probes, in pp. 18–30, *Nucleic Acid Hybridization: A Practical Approach* (Ed Hames and Higgins, IRL Press, 1985); or, in *PCR Protocols*, Chapters 18–20 (Innis et al., ed., Academic Press, 1990).

Those skilled in the art will know that the PCR process is most usually carried out as an automated process with a thermostable enzyme. In this process, the reaction mixture is cycled through a denaturing temperature range, a primer annealing temperature range, and an extension temperature range. A machine specifically adapted for use with a thermostable enzyme is disclosed more completely in EP No. 236,069, which is incorporated herein by reference, and is commercially available from PECI.

The ligase chain reaction is described in PCT Patent Publication No. WO 89/09835, which is incorporated herein by reference. The process involves the use of ligase to join oligonucleotide segments that anneal to the target nucleic acid. Ligase chain reaction (LCR) results in amplification of an original target molecule and can provide millions of copies of product DNA. Consequently, the LCR results in a net increase in double-stranded DNA. The present detection methods are applicable to LCR, as well as PCR. LCR requires an oligonucleotide probe for detecting the product DNA. When used in conjunction with the disclosed methods for detecting amplification products, a probe step is unnecessary, and the LCR result is immediately detectable.

Another amplification scheme exploits the use of the replicase from the RNA bacteriophage Qβ. In this amplification scheme, a modified recombinant bacteriophage genome with a sequence specific for the targeted sequence is initially hybridized with the nucleic acid to be tested. Following enrichment of the duplexes formed between the bacteriophage probe and the nucleic acid in a sample, Qβ replicase is added, which, upon recognizing the retained recombinant genome, begins making large numbers of copies.

The Qβ system does not require primer sequences and there is no heat denaturation step as with the PCR and LCR amplification systems. The reaction occurs at one temperature, typically 37° C. The preferred template is a substrate for the Qβ replicase, midvariant-1 RNA. A very large increase in the templates is achieved through the use of this system. A review of this amplification system can be found in the International Patent Application Pub. No. WO 87/06270 and in Lizardi et al., 1988, *Bio/Technology* 6:1197–1202.

The 3SR system is a variation of an in vitro transcription based amplification system. A transcription-based amplification system (TAS) involves the use of primers that encode a promoter to generate DNA copies of a target strand and the production of RNA copies from the DNA copies with an RNA polymerase. See, e.g., Example 9B of U.S. Pat. No. 4,683,202 and EP No. 310,229. The 3SR System is a system which uses three enzymes to carry out an isothermal replication of target nucleic acids.

The system begins with a target of single-stranded RNA to which a T7 RNA DNA primer is bound. By extension of the primer with reverse transcriptase, a cDNA is formed, and RNAseH treatment frees the cDNA from the heteroduplex. A second primer is bound to the cDNA and a double stranded cDNA is formed by DNA polymerase (i.e., reverse transcriptase) treatment. One (or both) of the primers encodes a promoter, i.e., the promoter for T7 RNA polymerase, so that the double-stranded cDNA is transcription template for T7 RNA polymerase.

Transcription competent cDNAs yield antisense RNA copies of the original target. The transcripts are then converted by the reverse transcriptase to double standard cDNA containing double-stranded promoters, optionally on both ends in an inverted repeat orientation. These DNAs can yield RNAs, which can reenter the cycle. A more complete description of the 3SR system can be found in Guatelli et al., 1990, *Proc. Natl. Acad. Sci. USA* 87:1874–1878, and EP No. 329,822, both of which are incorporated herein by reference. The TAS system is also described in Gingeras et al. in Innis et al. eds., 1990, *PCR Protocols*, Academic Press, San Diego, which is incorporated herein by reference.

The embodiments of the invention exemplified herein disclose the process for detecting amplified nucleic acids in conjunction with PCR. Accordingly, when used in a PCR-based method, the DNA binding agent is characterized as an agent that will not prevent primer annealing, primer extension along a complementary template, or strand separation of a DNA duplex.

In the process described herein, a sample is provided which contains, or is suspected of containing, a particular oligonucleotide sequence of interest, the "target nucleic acid." The target may be RNA or DNA or an RNA/DNA hybrid. The target may be single stranded or double stranded. Target preparation will be carried out in a manner appropriate for the particular amplification process to be implemented. For example, in a PCR method where the target nucleic acid is single-stranded DNA, such as mRNA, the target may be first reverse-transcribed into cDNA, prior to amplification.

Methods for reverse transcribing RNA into cDNA are well known and described in Maniatis et al., supra. Alteratively, preferred methods for reverse transcription utilize thermoactive DNA polymerases. These methods are described in commonly assigned, copending, U.S. Ser. No. 455,611, filed Dec. 22, 1989, and incorporated herein by reference. U.S. Ser. No. 455,611 describes a procedure for coupled reverse transcription/amplification of an RNA template using a thermostable DNA polymerase. The present specification teaches that intercalating agents do not prevent DNA polymerase activity. Consequently, the present method provides a homogeneous detection assay for RNA targets as well as DNA targets.

In another embodiment of the present invention, nested primers are used (Mullis et al., 1986, *Cold Spring Harbor Symposium on Quantitative Biology* 51:263, incorporated herein by reference). This method may be preferred when the amount of nucleic acid in a sample is extremely limited, for example, where archival, paraffin embedded samples are used. When nested primers are used, the nucleic acid is first amplified with an outer set of primers. This amplification reaction is followed by a second round of amplification cycles using an inner set of primers. Examples VI and VII describe modifications of nested primer methods that provide superior results without necessitating the additional sample handling required by using nested primers in successive rounds of amplification cycles.

According to the present invention, the generation of amplification products can be monitored while the reaction is in progress. An apparatus for detecting the signal generated by the binding agent, can be used to detect, measure, and quantify the signal before, during, and after amplification. Of course, the particular type of signal may dictate the choice of detection method. For example, in a preferred embodiment of the invention, fluorescent DNA binding dyes are used to label PCR products. The dyes intercalate, or bind, the double-stranded PCR products, and consequently, the resulting fluorescence increases as the amount of double-stranded DNA increases. The amount of fluorescence can be quantitated by measurement using a spectra-fluorometer with or without opening the PCR vessel. Examples VII and VIII demonstrate this aspect of the invention.

In Example VIII the fluorescence of the positive control sample was well above background measurements. Because signal generation was measured without having to open the reaction tube, this method of detection is readily adaptable to an automated format in which signal is monitored throughout the amplification process. Example VIII demonstrates an automated, on-line PCR detection method: a fiber optic lead was used to input excitation light directly to a PCR tube in a heating/cooling block. The same fiber optic was used to return fluorescent emissions back to the spectra-fluorometer, where the value was read.

In preferred methods for PCR, the amplification reaction is carried out as an automated process. A thermocycler currently available from Perkin Elmer Cetus Instruments uses a heat block capable of holding up to 48 reaction tubes. Consequently, 48 amplification reactions can be carried out simultaneously. The present invention permits PCR product detection in all 48 samples, without handling the samples, opening tubes, or interrupting the cycling reaction. A suitable optical system moves the excitation light from the source to the reaction tube and measures the emission light from each tube. For example, multiple fiber optic leads simultaneously read all PCR tubes undergoing thermocycling. However, only a single fluorometer is needed to read fluorescence from the reaction tubes, as each fiber optic can be read rapidly one at a time, for example, during the time frame of a PCR temperature soak. Alternatively, it will be obvious to one skilled in the art that such a detection system is not necessarily limited to a particular thermocycler machine or number of reaction vessels. However, the description of the 48 well PECI thermocycler serves to demonstrate this aspect of the present invention.

So long as the reaction wells, or tubes, are light sealed to prevent external light sources from influencing fluorescence detection, any over plate, tube cap, or lid apparatus that comprises or can be attached to, a fiber optic lead is suitable. In the embodiment of the invention at Example VIII, the reaction tube lids were removed to accommodate the fiber optic. However, use of a reaction vessel that has a clear or translucent cap eliminates the need to insert the cable into the tube. It will be apparent that reaction tubes able accommodate a fiber optic cable, without the cable physically contacting the amplification reaction components, is desirable. In a spectrafluorometer capable of heating and cooling a surface, or vessel, an optic fiber is not required. The optic fiber is only necessary where a thermocycler and spectrafluorometer are housed independently.

An analogous detection scheme is suitable in a 96-well microtiter format. This type of format is frequently desirable in clinical laboratories for large scale sample screening, for example, for genetic analysis such as screening for sickle-cell anemia or the AIDS virus in blood bank screening procedures. The present invention is suitable for this type of analysis and eliminates the need for the numerous washing and extraction procedures that are required with known "in-well" assay procedures such as ELISA type formats or other optical density-based methods. (See Kolber et al., 1988, *J. of Immun. Meth.* 108:255–264, Huschtscha et al., 1989, *In Vitro Cell and Dev. Biol.* 25(1): 105–108, and Voller et al., 1979, *The Enzyme Linked Immunosorbent Assay*, Dynatech Labs, Alexandria, Va.).

The present detection methods also allow direct fluorescence measurement using an apparatus similar to ELISA plate reader, but designed to excite and measure fluorescence. For example, the CytoFluor™ 2300 machine manufactured by Millipore is suitable in such a method. It is appropriate to "read" the microtiter plate before and after thermocycling for determining background fluorescence. Alternatively, an apparatus providing a continuous determination of fluorescence is useful for monitoring the increase in PCR product during the amplification reaction.

In another embodiment of the invention, following amplification, the size of the amplified product is determined without the use of a probe or size fractionation methods such as HPLC or gel electrophoresis. Copending U.S. Ser. No. 601,840, filed Oct. 23, 1990, which is incorporated herein by reference, describes a method for determining the average molecular weight of a PCR product using light scattering. The method is suitable for use in conjunction with the present invention especially when the homogeneous assay result is detected using a spectra fluorometer. A fluorometer reads emissions at the fluorescence wavelength, according to the present invention, and measures light scattering, for example, at a 180° angle. This aspect of the invention is particularly useful for determining if amplification has occurred and simultaneously distinguishing the amplified target product from, for example, primer-dimer and high molecular weight DNA.

In a preferred embodiment of the invention, the detectable binding agent is an intercalating fluorescent dye. The present examples describe that ethidium bromide is included in the amplification reaction mixture. Ethidium bromide, like other DNA binding dyes, such as acridines, proflavine, acridine orange, acriflavine, fluorcoumanin, ellipticine, daunomycin, chloroquine, distamycin D, cbromomycin, homidium, mithramycin, ruthenium polypyridyls, and anthramycin, exhibit altered fluorescence emissions when bound to double-stranded DNA. In an amplification reaction, a large amount of double-stranded DNA is generated from a starting template. Consequently, when this occurs in the presence of an intercalating fluorescent dye, a net increase in DNA-dependent fluorescence results. The target specificity of PCR and the use of appropriate positive and negative controls ensure that a detectable increase in fluorescence is due to the presence of the amplified target nucleic acid.

The present specification incudes several examples demonstrating various aspects of the homogeneous detection assay. The particular embodiments describe that ethidium bromide is present in the PCR at a concentration of 0.53 to 1.27 $\mu$M although a concentration of 0.08 $\mu$M (0.03 $\mu$g/ml) to 40.6 $\mu$M (16 $\mu$g/ml) is also suitable; however, an ethidium bromide concentration in the PCR mix in the range of 0.15 $\mu$M (0.06 $\mu$g/ml) to 20.3 $\mu$M (8 $\mu$g/ml) is preferred. It will be readily apparent to those of ordinary skill in the art how to determine a suitable concentration of alternative DNA binding agents by empirical adjustment. A suitable concentration of agent is any amount that provides a signal that is distinguishable when a net increase in double-stranded DNA has occurred in an amplification reaction. Consequently, the preferred concentration of agent included in the amplification reaction mix may vary depending on the amount of double-stranded non-target DNA (i.e., background genomic DNA), the copy number and amount of target, the quantity and fluorescence of the amplification primers and the particular agent utilized. For example, a standard curve using a known amount of target and varying the amount of binding agents may be appropriate. The fluorescent dye is added to the PCR mixture before starting temperature cycling. A suitable fluorescent dye does not prevent amplification from occurring. It will be obvious to one of ordinary skill in the art to determine the suitability of any novel dye in the method. Example I demonstrates that PCR amplification occurs in the presence of detectable amounts of ethidium bromide.

The emission spectrum of ethidium bromide peaks at 650 nm for unbound ethidium bromide and at 611 nm when the agent is bound to double-stranded DNA. However, because the emission spectra of bound and unbound ethidium bromide have distinct peaks, with bound ethidium emitting at a lower wavelength, discrimination between bound and unbound ethidium is enhanced by detecting emission at a non-peak wavelength that is less than the peak for bound ethidium. In the disclosed embodiment at Example VII, the fluorescence emission of the sample was detected at 570 nm. At Example VIII, the excitation wavelength was set at 500 nm and emission detection was set at 570 nm.

It is not essential that the detection or excitation wavelength is optimized for practice of the invention. For example, in Example II, a U.V. light box with an excitation wavelength at 300 nm and detection by photography through a red filter is suitable. A spectra fluorometer, depending on the features of the particular machine utilized, offers the opportunity to set the excitation and emission wavelength, as well as bandwidth. It will be obvious to one of ordinary skill in the art how to determine the wavelength and bandwidth settings for a particular DNA binding agent to be detected. Thus, although each agent has a discrete fluorescence spectrum, a broad range of detection wavelengths are suitable for practicing the invention, as exemplified herein. General guidance is found in, for example, The Merck Index, (eds. Budavari et al., 1989, Merck Co. Inc. Rahway, N.J.) where peak emission wavelengths for particular fluorescent agents bound and unbound to helical DNA are described at each entry. Similarly, the Molecular Probes, Inc. (Eugene, Oreg.) Catalogue, 1990, by Haugland is a suitable reference for describing DNA binding agents useful in the present invention.

In general, it is preferred but not essential that the DNA polymerase is added to the PCR reaction mixture after both the primer and template are added. Alteratively, for example, the enzyme and primer are added last or the PCR buffer or template plus buffer are added last. It is generally desirable that at least one component that is essential for polymerization not be present until such time as the primer and template are both present, and the enzyme can bind to and extend the desired primer/template substrate (see U.S. patent application Ser. No. 481,501, filed Feb. 16, 1990, which is incorporated herein by reference).

Commonly assigned, copending application U.S. Ser. No. 609,157, filed Nov. 2, 1990, and incorporated herein by reference, describes improved methods for reducing the effects of cross contamination of amplification reactions. The methods require the introduction of unconventional bases into the amplified product and exposing carryover to enzymatic and/or physical chemical treatment which effectively render the product incapable of serving as a template for subsequent amplifications. The homogeneous detection assay described herein is suitable in conjunction with the sterilization methods described in U.S. Ser. No. 609,157. These methods enhance the accuracy and reliability of amplification results by eliminating steps, and thereby minimizing product handling, which reduces carryover. The sterilization method provides additional assurance that carryover template is eliminated.

Preferably, the DNA binding agent is storage stable and can be included as a component in a PCR reagent buffer. Thus, the invention provides novel reagents suitable for commercialization in a kit format. Such a reagent may contain a solution of the DNA binding agent in a kit for detecting nucleic acids by PCR. Alteratively, the reagent might contain a DNA binding agent, as well as other PCR buffer components such as Tris-HCl, KCl, and $MgCl_2$, each in appropriate concentrations for carrying out PCR. In one embodiment, a kit includes a buffer comprising ethidium bromide at a suitable concentration to provide, in an amplification reaction, a final ethidium bromide concentration in the range of 0.15 $\mu$M to 20.3 $\mu$M. The buffer may additionally contain any or all of the following reagents: Tris-HCl, pH 8.0–8.3; KCl, and $MgCl_2$ each in appropriate concentrations for PCR amplification. Kits for detecting amplified nucleic acids are also envisioned as including any of the following: an agent for polymerization, dNTPs, appropriate primers, and a positive control template. The '202 patent describes methods for preparing and using primers for PCR which have non-complementary sequences added to the 5' end. These "tails" are useful for engineering particular restriction sites or other purposes, because during PCR, the non-complementary tail sequence is incorporated into the double-stranded PCR product. Particular tail sequences provide binding targets for specific dyes. For example, Hoechst 33258 (Searle and Embrey, 1990, *Nuc. Acids Res.* 18:3753–3762) preferentially binds A-T base pairs. A PCR primer synthesized with a long A-T rich 5' tail provides a relatively A-T rich PCR product in comparison with genomic DNA. Using Hoechst 33358 the A-T rich PCR product has increased fluorescence relative to genomic DNA and, consequently, is useful for increasing signal strength in the presence of genomic DNA.

Similarly, DAPI forms a fluorescent complex with AT rich DNA (see Kapuseinski & Szer, 1979, *Nuc. Acids Res.,* 6(112):3519). In contrast, Actinomycin D forms a fluorescent complex with G-C rich DNA (Jain and Sobell, 1972, *J. Mol. Biol.* 68:21). Thus, the present invention is suitable for monitoring the amount of two distinct target nucleic acids in one reaction vessel, by including two fluorochromes in the reaction mixture during amplification. It is only necessary that one fluorochrome has sequence specificity and that sequence is included in the tail (i.e., 5' end) of a primer to one of the two target nucleic acids. The emission spectra for each fluorochrome is separately determined during and/or after amplification by a spectra fluorometer. Thus, the invention is particularly useful for quantitative comparisons of two different nucleic acid targets in the same sample and as such may be useful for determining the extent of, for example, an infection or disease if one target is a sequence present in all cells and the other is present in a pathogen.

Similar agents with distinct binding properties permit multiplex PCR methods for detecting several targets in one sample without ever opening the reaction vessel once the amplification reaction is initiated. Fluorescent DNA binding dyes may each have different emissions and excitation spectra. In a clinical setting, different DNA binding dyes having different DNA sequence specificities are useful for indicating the presence of distinct targets.

Methods for quantitating nucleic acids are described in commonly assigned, copending U.S. Ser. Nos. 254,889, filed Oct. 7, 1988, and 413,623, filed Sep. 28, 1989. These applications are incorporated herein by reference. These applications describe PCR-based methods using an internal standard to determine either the relative amount of a target or accurately quantitate the amount of target present prior to amplification, respectively. The present invention is suitable in conjunction with the methods described in the '889 and '623 applications.

In another embodiment, the present invention provides means for determining the intactness of a DNA sample. For example, forensic analysis often involve samples containing partially degraded target, such as an archival sample. The ability to monitor the generation of PCR product, demonstrated in Example VIII, allows comparison of the amplification profile of a DNA sample with respect to a small PCR product and a large PCR product, in separate reactions. If there is no degradation, monitoring the increase in double-stranded DNA shows that both reactions reach plateau at approximately the same cycle. If there is degradation, the small product would reach plateau sooner than the large fragment due to the presence of more intact target molecules.

It will be apparent to those of ordinary skill in the art that the homogeneous detection assay provided herein is suitable for a wide variety of applications, including, for example, genetic screening, forensic human identification, pathogen detection, and quantitation, environmental monitoring or tagging and tracing materials with nucleic acid (see, for example, U.S. Ser. No. 355,455, filed May 22, 1989, which is incorporated herein by reference).

In one embodiment, the detectable signal is fluorescence. Fluorescence is suitable for use in qualitative as well as quantitative methods. Qualitative detection can be made simply and rapidly by visual inspection of the reaction tubes by exposure to UV light. This type of rapid, highly sensitive assay is desirable as a rapid screen for the presence of a pathogen or of a particular gene sequence causative of or associated with a disease state. The present invention provides means for cutting costs by a plus/minus pre-screen for the presence of any member of a group of targets. Amplifications for many different such targets would allow this if it may be expected that most samples are negative, e.g., environmental monitoring for pathogen detection systems. Multiplex PCR is a process for including a number of distinct primer pairs in one amplification reaction (see, Gibbs et al.,1989, in *PCR Technology* ed. Erlich, Stockton Press, N.Y.)). A homogeneous detection assay using multiple primer pairs to assay a wide range of potential targets is then followed by more complex typing procedures only on positive samples. This pre-screen saves the cost of performing the more complex typing procedure on negative samples and/or performing repeated tests on negative samples.

The present methods for homogeneous detection of target nucleic acids are also suitable for quantitation of a particular target. Whether the methods are automated or manually performed, quantitation can be accomplished by a number of means. For example, a serial dilution of the sample, in parallel with a serial dilution of a known standard, provides a series of templates, which, following PCR and signal detection, are suitable for quantitating the amount of starting material in the known sample. Similarly, because fluorescence can be determined between cycles during the course of a PCR, the exponential phase of PCR and the cycle at which the level of product reaches the plateau phase, can be readily determined. The more target DNA present at the start of PCR, the sooner the reaction reaches plateau, i.e., the point when the rate of product accumulation begins to diminish. Because the number of cycles needed to reach plateau is directly related to the amount of target present in the sample, monitoring fluorescence while PCR is in progress serves to quantitate small amounts of DNA.

The invention is suitable for detecting amplified nucleic acids in the presence of double-stranded genomic DNA. Background levels of DNA as high as 0.5 $\mu$g or more will not obscure a positive assay result. The target nucleic acid can be a cloned segment, a repeat sequence, such as a multi-copy gene or tandem repeat, a single copy gene, or an infectious agent present in a concentration as low as one copy per 70,000 cells. The starting template is RNA or DNA because PCR provides a net increase in double-stranded nucleic acid starting from either template nucleic acid.

The target nucleic acid may be a rare sequence, such as a single copy of AIDS virus DNA in a background of human genomic DNA from more than 70,000 cells. In such an instance, procedures for increasing specificity serve to insure that amplification provides a net gain in double-stranded DNA only in response to the presence of the target sequence, and that net gain is detectable in the presence of high background of genomic DNA. U.S. Pat. No. 4,683,195 demonstrates the use of nested primers to decrease the background in the amplification of single copy genes.

The procedure for nested amplification in U.S. Pat. No. 4,683,195 requires a first primer pair to amplify a target sequence and a second primer pair to amplify a subsegment of the PCR product formed from the first amplification reaction. Following the first PCR, the reaction mixture is diluted 10-fold to reduce the concentration of the first primer pair, and the second primer pair is introduced into the reaction mixture. However, because a particular advantage of the present invention lies in the elimination of steps, the additional steps of stopping an amplification reaction to dilute the sample and adding a second primer pair are not desirable.

To address this issue, modified nested amplification procedures are provided. The present nested primer methods are vastly improved over prior nested primer procedures for amplifying nucleic acids. These methods provide enhanced specificity and are applicable in any PCR-based amplification scheme. However, in the present disclosure, these procedures are described used in a homogeneous assay.

In one modified nested primer method, a third primer, internal to a flanking pair of PCR primers is included in a PCR reaction for amplifying a particular target segment. The third primer has an annealing/melting temperature, when it is hybridized to its complementary target strand, that is lower than that of the flanking primer. This property can be imparted to the primer by a shorter length and/or lower G-C content. For the first 15–20 PCR cycles, the temperature during the extension phase of each PCR cycle is maintained sufficiently high, i.e. approximately 65° C. to prevent the short primer from annealing specifically and initiating amplification. The flanking primers anneal sufficiently such that PCR proceeds normally at the high extension temperature. However, the primer flanking the third primer is present at a low concentration. In the method, prior to amplification plateau, when the supply of limiting primer is almost exhausted, the annealing temperature is decreased to approximately 42° C. At this temperature, the third primer "drops in" and proceeds to amplify the target for the remaining 15 or so cycles.

In an alterative method for nested primer amplification, the need for a low concentration of one primer is eliminated. The flanking primer is synthesized with a G-C rich tail. Because the non-complementary primer tail sequence is incorporated into the PCR product after two cycles of amplification, the G-C tails serves to raise the temperature necessary for denaturing the PCR product because of the increased thermostability of G-C pairs versus A-T pairs. (See Myers et al., 1989, in PCR Technology ed. Erlich, Stockton Press, New York, which is incorporated herein by reference). The resulting difference in the denaturing temperature between the nested and flanking PCR product is then exploited to effectively shut down amplification from the tailed flanking primer. Once PCR product is made from the flanking primers, the denaturation temperature is lowered, i.e., from 96° C. to 86° C., so that the temperature is too low for amplification of the flanking PCR product, but is high enough to allow amplification of the nested PCR product. The annealing temperature may also be manipulated, as in the "drop-in" method, to initiate synthesis from the nested primer when desired.

It would be obvious to one of ordinary skill in the art to empirically determine the appropriate denaturation and annealing temperatures and program a thermocycler accordingly. This "drop-out primer" method provides means for including high concentrations of the flanking primer to maintain PCR efficiency, and allow the amplification initiated by that primer to be terminated during the reaction as desired. This particular method for nested primer amplification is demonstrated in Examples VI and VII.

The following examples serve to illustrate various aspects of the present invention and are not intended as a limitation.

EXAMPLE I

PCR in the Presence of Ethidium Bromide

This example demonstrates the ability of PCR to proceed in the presence of ethidium bromide.

Two PCRs were carried out as follows. Each 100 µl PCR contained: 50 ng human DNA, 10 mM Tris-HCl pH 8, 50 mM KCl, 4 mM $MgCl_2$, 250 µM each dNTP, 2.5 units Taq polymerase (Perkin-Elmer Cetus Instruments, Norwalk Conn.), 20 picamole each primer GH26 (SEQ ID NO: 1) and GH27 (SEQ ID NO: 2). The human DNA was purified from a human B-cell line. DNA was prepared according to the method described by Maniatis (supra). An oil overlay was added to each reaction to prevent evaporation.

The two PCRs were conducted under identical conditions except that 0.51 µM of ethidium bromide (Sigma) was included in one reaction. A thermocycler purchased from Perkin-Elmer Cetus Instruments was programmed with the following cycling parameters; denature at 96° C., hold for 1 minute, anneal at 55° C., hold for 1 minute, extend at 72° C., hold for 1 minute. This profile was repeated for 32 cycles. After amplification 5 µl of each PCR was analyzed by gel electrophoresis using a 3% NuSieve agarose gel (FMC). The gel was stained with ethidium bromide by standard methods and the amount of PCR product made in the two reactions was compared. The results demonstrated that the amount of amplified DNA produced in the presence of ethidium bromide was indistinguishable from the amount of PCR product made in the absence of the dye. Additionally, the specificity of the PCR, measured by the ability to produce DNA fragments of the expected size, was unchanged.

EXAMPLE II

The Specificity of PCR is Sufficient for Fluorescence-Based, Homogeneous Detection of Target Nucleic Acids The experiment described in Example I was expanded upon to determine whether target specific ethidium bromide fluorescence is readily visible using standard PCR conditions. Therefore, five 100 µl reaction mixtures were prepared containing 10 mM Tris-HCl pH8, 50 mM KCl, 2.5 mM $MgCl_2$ 1.27 µM ethidium bromide, 150 µM each dNTP, 2.5 units Taq polymerase. Primers and target DNA were included as described below. Primer pair GH15 (SEQ ID NO: 3) and GH16 (SEQ ID NO: 4) are specific for amplifying DQα and do not amplify DRβ1 target DNA. DQα target DNA was prepared by amplifying the human DQα gene as described in Example I. Following amplification, the DQα PCR product was diluted to provide ~$2\times10^7$ copies (5 pg) of amplified DNA per amplification. The DQα product was used as a positive control. DRβ1 target DNA was prepared using primer pair GH46 (SEQ ID NO: 5) and GH50 (SEQ ID NO: 6) to amplify the DRβ1 gene in a PCR using human genomic DNA. The PCR product was diluted to provide ~$2\times10^7$ copies of DRβ1 DNA and used in Reaction 4, below, as a negative control. The five reaction mixtures contained primers and target as follows:

Reaction 1—No primers+DQα Target
Reaction 2—Primers+DQα target
Reaction 3—Primers+DQα target
Reaction 4—Primers+DRβ1 target
Reaction 5—Primers+no target Where primers were included 10 pmoles each of GH15 (SEQ ID NO: 3) and GH16 (SEQ ID NO: 4) were added. Reaction mixtures 1 and 2 were not subjected to amplification cycles. Reactions Nos. 3, 4, and 5 were subjected to 20 cycles of amplification. The cycling parameters were 94° C., hold for 1 minute; 45° C., hold for 1 minute; and 72° C., hold for 1 minute.

The reaction tubes were then placed on a UV light box (300 nm) and photographed for two seconds and one-half second exposures. The results, shown in FIG. 1, demonstrated the increased fluorescence in Reaction No. 3 due to the amplification of the specific target DNA. Reaction Nos. 1 and 2 indicated the level of fluorescence present before any amplification occurred. Reaction Nos. 4 and 5 demonstrated that fluorescence does not increase visibly in a reaction unless, for the particular primer pair present in the reaction, an appropriate template is also present. The different photographic exposures demonstrate the relative differences in fluorescence (FIG. 1).

EXAMPLE III

The Simultaneous Ethidium Bromide Detection and Amplification of Specific DNA Sequences in the Presence of Genomic DNA The ability of the present homogeneous assay method for detecting a specific target in the presence of non-target double-stranded DNA was tested. This example demonstrates detection of a specific DNA sequence in a background of genomic DNA. Twenty 100 µl PCR mixtures were prepared as follows. Each contained 10 mM Tris-HCl, pH 8; 50 mM KCl; 2 mM MgCl$_2$; 2.9 units Taq polymerase; 180 µm each dNTP; 1.27 µM ethidium bromide; 15 picamole RH191 (SEQ ID NO: 7); and 15 picamole RH192 (SEQ ID NO: 8). The primers RH191 (SEQ ID NO: 7) and RH192 (SEQ ID NO: 8) are derived from primers y1.1 and y1.2, which are described in Kogan et al., 1987, *N. Engl. J. Med.*, 317:985–990, which is incorporated herein by reference. These primers are specific for a human male-specific sequence that occurs in several thousand copies per human male cell. Fifteen PCR reaction mixtures were set up as follows. Sample DNA was prepared from human blood taken from a male or female as specified for each reaction. DNA was prepared according to Maniatis supra.

Reaction Nos. 1–5 contained 2 ng human male DNA

Reaction Nos. 6–10 contained no DNA

Reaction Nos. 11–15 contained 60 ng human female DNA

Reaction Nos. 16–20 contained 60 ng human male DNA

The reactions were all placed in a Perkin-Elmer Cetus Instruments thermocycler programmed to cycle at 94° C. for 1 minute; 60° C. for 1 minute, for the indicated number of cycles. As indicated below, tubes were removed from the thermocycler at various cycles to provide a PCR time course for each template. Specifically, for each set of five tubes, 0, 17, 21, 25, and 29 amplification cycles were performed. PCR product was detected by exposing the tubes to UV-light as described above.

By photography and visual inspection, Tube Nos. 6–15 exhibited no increase in fluorescence. Tube Nos. 1 and 2, the 0 and 17 cycle male DNA samples, also had no increase in fluorescence by visual detection. Only the 21, 25, and 29 cycle male DNA reactions fluoresced under UV light, and the amount of fluorescence increased with increasing cycle number. The results with Tube Nos. 16–20 were similar, except that an increase in fluorescence was noted by 17 cycles. This is consistent with the presence of more copies of the target DNA sequence present in the sample prior to amplification.

EXAMPLE IV

Quantitative Measurement of Target Specific Ethidium Bromide Fluorescence

Figure 2:
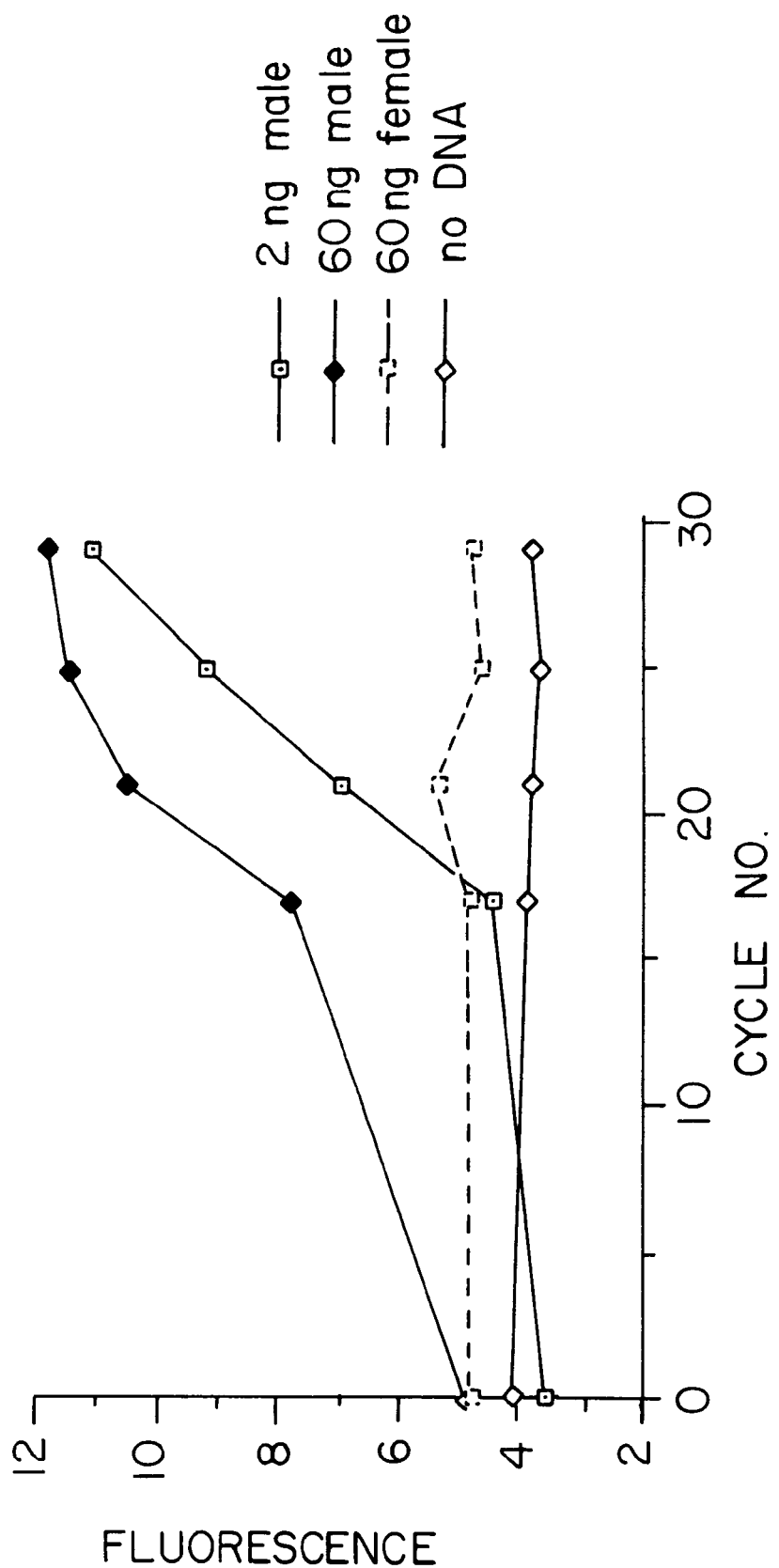
FIG. 2 demonstrates the target specificity of the present detection method and illustrates some of the quantitative aspects of the invention. The details of the experiment are provided at Example IV.

The reactions of Example III were opened, and the contents transferred to a spectra fluorometer (SPEX Fluorolog-2, purchased from Spex, Edison, N.J.) which was used to get a quantitative fluorescence value for each reaction. The results shown in FIG. 2 not only demonstrate the target specificity of the detection method but illustrate the quantitative aspects of the invention. The effect of increased target in the sample is observable by comparing the time course of fluorescence between the 2 ng and 60 ng male templates. The more target DNA in the sample, the sooner the reaction obtains a measurable increase in fluorescence and finally reaches a plateau level of fluorescence. Exactly when the reaction fluorescence begins to increase measurably is effectively a quantitative measure of how much target was present prior to amplification.

EXAMPLE V

Detection of a Single Copy Gene

This example demonstrates the suitability of the homogeneous assay not only for detecting a single copy gene among total human genomic DNA, but for discriminating among two alleles of that single copy gene present in the sample that differ by a single nucleotide. (Methods for allele specific detection are described in detail in European Patent Publication No. 237,362, which is incorporated herein by reference).

The particular gene to be detected is the β-globin gene. A single base pair change mutates a wild-type β-globin allele into a sickle cell allele. In this example, the following primers were used: RH187 (SEQ ID NO: 9), RH188 (SEQ ID NO: 10), and RH189 (SEQ ID NO: 11). Primer pair RH187/RH188 (SEQ ID NO: 9/SEQ ID NO: 10) specifically amplified the wild-type allele. Primer pair RH187/RH189 (SEQ ID NO: 9/SEQ ID NO: 11) amplify the sickle cell allele (these primers derive from BGP2, Hβ14A, and Hβ14S described in Wu et al., 1989, *PNAS (USA)*, 86:2757–2760, which is incorporated herein by reference). Six PCRs were set up as follows: 10 mM Tris-HCl, pH 8.3; 50 mM KCl; 748 µM total dNTPs; 2.9 units Taq polymerase; 10 pmoles each primer, 1.5 µM MgCl$_2$; 1.27 µM ethidium bromide, and 50 ng of human DNA template as follows: one pair of reactions contained human DNA homozygous for sickle allele (SS); one pair of reactions contained wild-type DNA (AA); and one pair contained heterozygous DNA, i.e., one wild-type and one sickle cell allele (AS).

For each pair of reactions, one tube contained primers specific for the sickle β-globin allele and one tube contained primers for the wild-type sequence. The only difference between the primer sets are the 3' nucleotides of one of the primer pairs, which match either the sickle cell or the wild-type target sequence. Primer annealing temperature during PCR is set such that amplification will occur only if this 3' nucleotide matches the template. The cycling parameters were: 94° C. for 60 seconds, 55° C. for 60 seconds.

Figure 3:
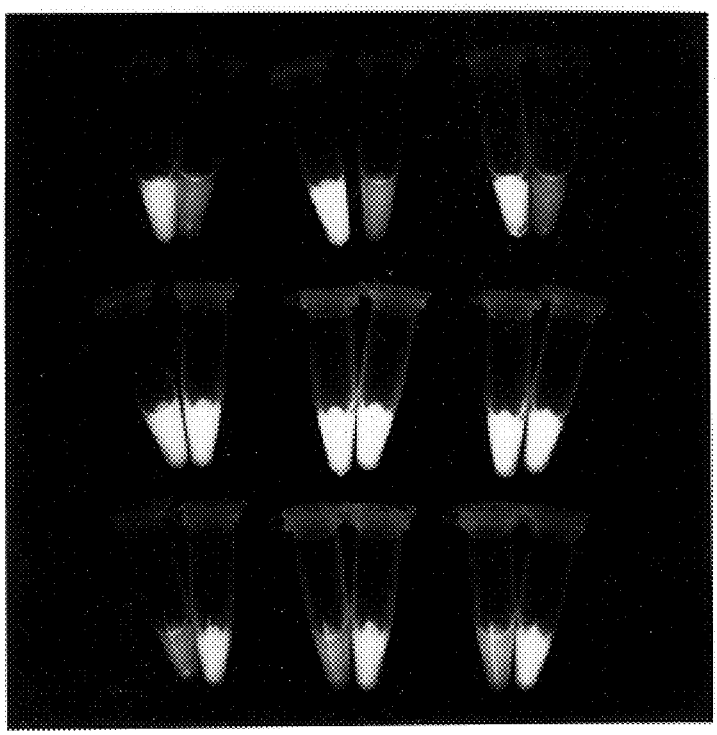
FIG. 3 demonstrates the use of the present invention for genetic screening. The experiment is described in detail at Example V.

The reaction was done in triplicate and after 30 cycles of PCR, the tubes were placed on a UV-light source and photographed (see FIG. 3). The results were as follows:

|  | Sickle β-globin Primers | Wild-type Primers |
| --- | --- | --- |
| Homozygous AA | − | + |
| Heterozygous AS | + | + |
| Homozygous SS | + | − |

A "+" indicates that fluorescence was readily visible under UV light, and when measured on a spectra-fluorometer the "+" tubes had approximately three times greater fluorescence than "−" reactions. The PCR's marked "−" did not change significantly in florescence as a result of the amplification reaction.

Aliquots of each reaction were analyzed by gel electrophoresis. Each "+" reaction exhibited a specific discrete DNA fragment. The "−" reactions had no such DNA fragment by gel analysis.

EXAMPLE VI

Detection of a Rare Target in the Presence of a High Background of Double-Stranded DNA A detection assay was designed to demonstrate the suitability of the present invention for detecting a rare target sequence in a background of DNA from approximately 70,000 human cells. A modified nested primer procedure, as briefly described in the "Detailed Description" section as a primer "drop-out" procedure, was designed to enhance PCR specificity. This assay was done as follows: into PCR reaction vessels 1 through 8 were aliquoted 50 microliters of solution, each containing 50 mM KCl; 10 mM TrisHCl, pH 8.3; 2.5 mM MgCl$_2$; 600 $\mu$M total dNTPs; 1.25 unit of Taq DNA polymerase (PECI); 1.27 $\mu$M ethidium bromide; 0.5 $\mu$g of human cell-line DNA; the primer pair RH171 (SEQ ID NO: 12) and RH176 (SEQ ID NO: 13), each primer at 0.2 $\mu$M; and the nested primer RH182 (SEQ ID NO: 14) also at 0.2 $\mu$M. A drop of mineral oil was used to cover the eight solutions in order to prevent evaporation. Primer RH176 (SEQ ID NO: 13) carries a GC-rich, non-homologous (to target sequence), 5' "tail" that raises the denaturation temperature necessary to amplify PCR product made using this primer.

Reactions 1–4 were made with solutions that were at ambient room temperature and included the three primers before temperature cycling was begun. Reactions 5–8 were made with the addition of the three primers postponed until these reactions were equilibrated to a temperature of 72° C. before beginning thermocycling. For this reason, reactions 5–8 are referred to as being given a "hot-start" Reactions 2–4 and 6–8 also contained a target, positive control DNA (purchased from PECI) containing HIV sequences to which RH171 (SEQ ID NO: 12), RH176 (SEQ ID NO: 13), and the 3' portion of RH182 (SEQ ID NO: 14) were homologous. This DNA was diluted such that each reaction containing it had, on average, four copies of the HIV sequence. Because this average number of copies is small, the actual number of copies in a given reaction can vary considerably. Since no HIV DNA target was added to reactions 1 and 5, these reactions served as negative controls.

All eight reactions were subjected to thermocycling as follows: denature at 96° C., hold for 1 minute, anneal at 64° C., hold for 1 minute. This profile was repeated for 29 cycles, during which the flanking primer pair, RH171 (SEQ ID NO: 12) and RH176 (SEQ ID NO: 13), efficiently annealed and were used in amplification, while the nested primer RH182 (SEQ ID NO: 14), which does not efficiently anneal at 64° C., was not used in efficient amplification. This was followed by denaturation at 96° C., hold for 1 minute, annealing at 52° C., hold for 1 minute. This profile was repeated for 2 cycles, during which all three primers efficiently annealed and were extended in amplification such that products were made using either RH171 (SEQ ID NO: 12) and RH176 (SEQ ID NO: 13), or RH171 (SEQ ID NO: 12) and RH182 (SEQ ID NO: 14). Because the use of a third, nested primer, increases product specificity, products made using RH171 (SEQ ID NO: 12) and RH182 (SEQ ID NO: 14) were more likely to be HIV specific. These cycles were followed by denaturation at 86° C., hold for 1 minute, anneal at 52° C., hold for 1 minute. This profile was repeated 18 times, during which, products that included the GC-rich primer RH176 (SEQ ID NO: 13), both HIV specific and non-specific, did not efficiently denature at 86° C. and, therefore, did not amplify efficiently, while the amplified HIV sequences made using the nested primer RH182 (SEQ ID NO: 14) and RH171 (SEQ ID NO: 12) did efficiently denature and amplify.

All eight reactions were analyzed, when completed, by gel electrophoresis. Reactions 2–4 and 5–8 were shown to contain a product of the expected size (approximately 200 bp) as the predominant band on the gel. Reactions 1 and 5, the negative controls, contained no such product. However, reactions 2–4, which were not given a "hot-start," could be seen to contain DNA fragments of other than the expected size. These other DNA fragments were also visible in reaction 1, indicating that they are not derived from HIV sequences. These other DNA fragments were not visible in reactions 5–8, indicating that use of the "hot-start" had enhanced the specificity of these reactions.

Eight additional reactions were performed as described above, except that all were given a "hot-start" as described above. The positive control DNA was diluted in these eight reactions, numbered 1 through 8, such that on average, each contains half an HIV target molecule. Since a molecule cannot be divided, this means that some reactions should contain a target molecule and some should not. If this experiment were repeated many times, the fraction of reactions that do contain a target will vary considerably, but should be on average about half. Those that do contain a target molecule are most likely to contain a single target molecule. Upon completion of the reactions, all eight were analyzed by gel electrophoresis. The result was that two of the eight reactions, numbers 1 and 8, displayed a DNA fragment of the expected size (approximately 200 bp) as the predominant band on the gel, with no other bands that migrated into the gel visible except a band corresponding to the primers. Reactions 2–6 displayed no such bands nor any other DNA fragment bands.

EXAMPLE VII

A Method for Quantitative Detection of PCR Product

A spectra-fluorometer Spex fluorolog-2 (Spex, Edison, N.J.) was used to quantitate the net increase in fluorescence generated in response to what is expected to be a single HIV target in the presence of genomic DNA. The spectra-fluorometer was used according to manufacture's specifications as described in Example VIII. The PCR reactions described in Example VI, in which positive control DNA was diluted among eight reactions to contain half an HIV target molecule per reaction, were analyzed for their fluorescence. Twenty $\mu$l of each completed reaction was added to 100 $\mu$l of 10 mM Tris HCl, pH 8, 0.1 mM EDTA, 1.27 $\mu$M ethidium bromide. The fluorescence of these solutions was measured at 570 nm. FIG. 4A graphically demonstrates the significant increase in fluorescence of the two positive samples compared to the two negative samples. In the figure, dotted lines mark the fluorescence values two standard deviations away from the average of the negative samples. The PCR-positive samples are both above this line.

The results are also shown in FIG. 4B using a background substraction method. The fluorescence up to the second standard deviation below the mean was subtracted from the detected values. Background subtraction is preferably performed by measuring fluorescence in each sample at the beginning of PCR cycling (preferably after the initial denaturation, which reduces the proportion of double-stranded genomic DNA) and subtracting that value from the fluorescence in the sample at the end of PCR cycling.

EXAMPLE VIII

A Method for Automated/On-Line Detection of PCR Product During Amplification

The following experiment demonstrates the suitability of the present method for monitoring a PCR reaction and detecting the net increase in double-stranded DNA due to amplification. The apparatus allows on-line detection of PCR product.

The apparatus was set up as follows: a Spex-Fluorolog-2 fluorometer with a fiber optic accessory (Spex Catalog No. 1950) was set to emit excitation light at 500 nm with a bandwidth of ~3.4 nm. A GG 435 nm cut off filter used to exclude second order light (Purchased from Melles Grist Inc.). The emission light was detected at 570 nm with a bandwidth of ~13.6 nm. A OG530 filter (530 nm cut off) was used to remove excitation light.

Two PCR reactions were set up as described in Example III using primers RH191 (SEQ ID NO: 7) and RH192 (SEQ ID NO: 8). One reaction tube contained 60 ng human male DNA, the other contained no target DNA. The reactions were set up in 0.5 ml polypropylene tubes; however, the top of the tubes was cut away for attaching the fiber optic cable. The fiber optic was glued to the top of the reaction tube with epoxy. Because this apparatus had one fiber optic, only one PCR was run at a time. The emission light was collected through the oil overlay in the tube. A black "shroud" was built around the tube and the reaction was placed in the thermocycler. The thermocycler was programmed to cycle between 94° C. and 50° C. for 1 minute each, for 30 cycles, followed by continuous incubation at 25° C. The fluorometer and thermocycler were started simultaneously. The parameters of the fluorometer were: time based scan with 5 second integration time; the emission signal was ratioed to that of the excitation light to control for changes in source intensity.

FIG. 5A shows the results of the PCR reaction containing no DNA. FIG. 5A shows that the thermocycler started at 25° C., the fluorescence dropped as the temperature increased to 94° C. and fluorescence increased again when the temperature decreased to 50° C. This pattern was repeated for the remaining cycles until the thermocycler again reached 25° C. and the fluorescence returned to the approximate starting value.

Figure 5B:
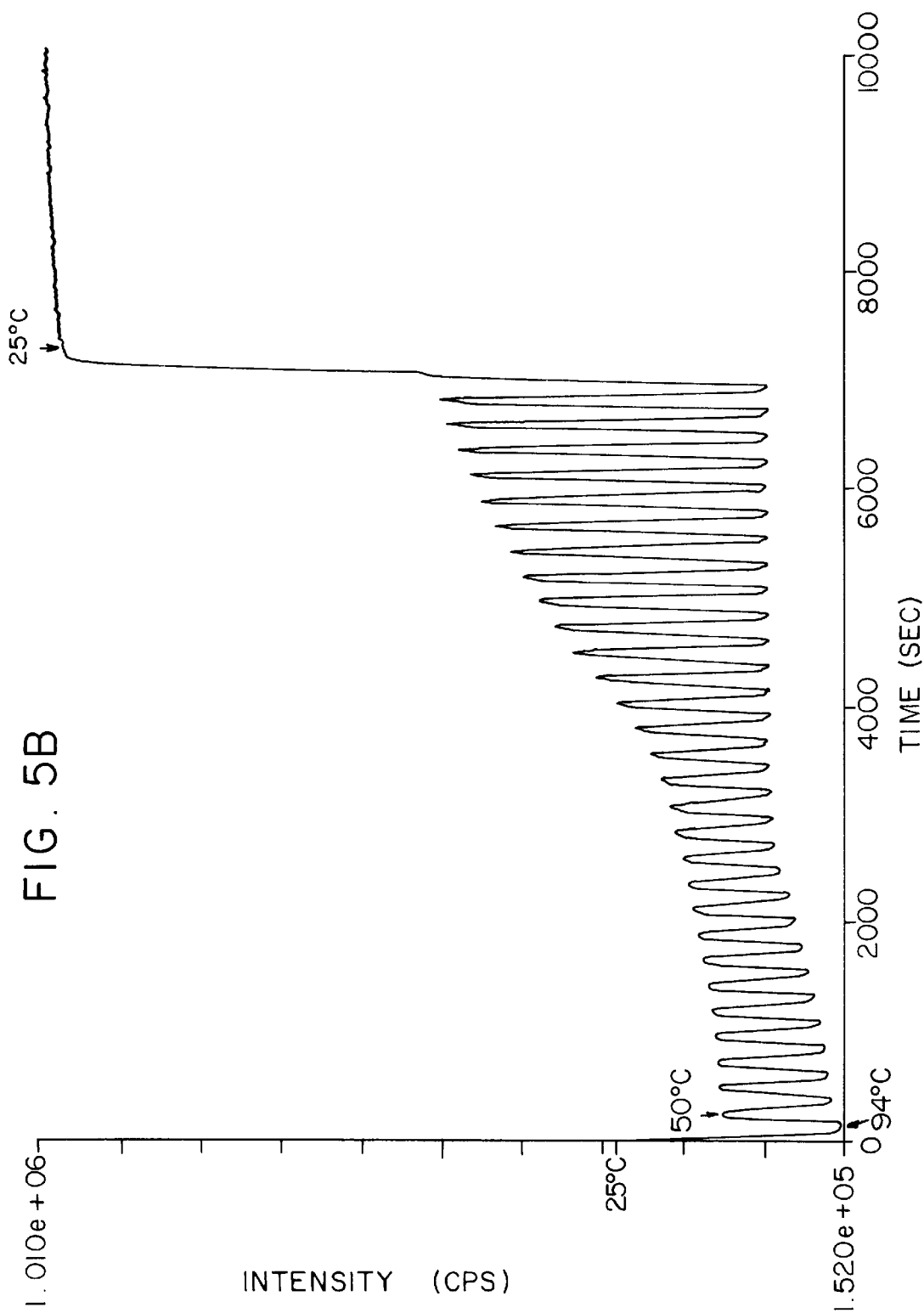

FIG. 5B demonstrates the fluorescence profile of a PCR reaction containing the appropriate target DNA. The fluorescence intensity at 50° C. shows a cycle dependent increase reflecting an increase in the amount of double-stranded DNA. When the thermocycler returned to 25° C., after the 30 cycles were completed, the fluorescence increased to a final value greater than three times the initial fluorescence value at 25° C.

Following amplification, an aliquot of each reaction mixture was analyzed by agarose gel electrophoresis. The gel analysis demonstrated that no PCR product was visible in the lane containing a sample from the negative control. The electrophoresed sample from the positive control PCR showed a clear and unique band at ~150 base pairs. The predicted size of the PCR product was 154 bp.

Thus, the on-line method provided a rapid analysis as to the presence or absence of target DNA without the need for probes or further processing steps. In addition, the continuous detection of fluorescence throughout the amplification provides an amplification profile that reflects the amount of target present at start. If the target DNA is, for example, a human repeat sequence present in millions of copies per cell (e.g., "Alu" sequences; Nelson and Caskey in *PCR Technology* ed. Erlich [1989], Stockton Press, N.Y.), this method of quantitation could be used to quickly and simply to measure sub-cellular amounts of DNA, which is at present difficult to do without using radioisotopes.

| Primer Sequences for Examples I-VIII | | |
|---|---|---|
| Cetus Nomenclature | SEQ ID NO | Primer Sequence |
| GH26 | 1 | 5' GTGCTGCAGG TGTAAACTTG TACCAG 3' |
| GH27 | 2 | 5' CACGGATCCG GTAGCAGCGG TAGAGTTG 3' |
| GH15 | 3 | 5' GTGTAAACTT GTACCAG 3' |
| GH16 | 4 | 5' GGTAGCAGCG GTAGAG 3' |
| GH46 | 5 | 5' CCGGATCCTT CGTGTCCCCA CAGCACG 3' |
| GH50 | 6 | 5' CTCCCCAACC CCGTAGTTGT GTCTGCA 3' |
| RH191 | 7 | 5' TCCACTTTAT TCCAGGCCTG T 3' |
| RH192 | 8 | 5' TTGAATGGAA TGGGAACGAA TGG 3' |
| RH187 | 9 | 5' AATAGACCAA TAGGCAGAG 3' |
| RH188 | 10 | 5' CACCTGACTC CTGA 3' |
| RH189 | 11 | 5' CACCTGACTC CTGT 3' |
| RH171 | 12 | 5' CCAGGCCAGA TGAGAGAACC AAGGGG 3' CGGTCTACAT AGTCTCTAAA GGG 3' |
| RH182 | 14 | 5' GGTCCCTGTC TTATGTC 3' |

Although the foregoing invention has been described in some detail for the purpose of illustration, it will be obvious that changes and modifications may be practical within the scope of the appended claims by those of ordinary skill in the art.

---

We claim:

1. A method for detecting a target nucleic acid in a sample, said method comprising:
   (a) providing a DNA amplification reaction mixture that comprises said sample, a DNA binding agent, wherein said agent is characterized as providing a detectable signal when bound to double-stranded DNA which signal is greater than the amount of said signal provided by said agent when it is unbound, and wherein said agent does not significantly inhibit the rate of nucleic acid amplification and reagents for amplification;
   (b) determining the amount of said signal produced by the mixture of step (a);
   (c) treating said mixture under conditions for amplifying said target nucleic acid to produce amplified double-stranded DNA;
   (d) determining the amount of said signal produced by said mixture of step (c); and
   (e) determining if amplification has occurred.

2. The method of claim 1, wherein said DNA binding agent is an intercalating agent.

3. The method of claim 2, wherein said intercalating agent is a fluorescent dye.

4. The method of claim 3, wherein at step (e) an increase in fluorescence indicates that amplification has occurred.

5. The method of claim 4, wherein at steps (b) and (d) the amount of signal produced is determined by exposing said mixture to UV light, and at step (e) comparing the relative amount of signal produced at steps (b) and (d) to determine if amplification has occurred.

6. The method of claim 4, wherein said fluorescent dye is ethidium bromide.

7. The method of claim 4, wherein the amount of signal produced is determined using a spectra fluorometer.

8. The method of claim 4, wherein said target nucleic acid is indicative of a genetic or infectious disease.

9. The method of claim 4, wherein the amount of target DNA in said sample, prior to amplification, is quantitated by determining the increase in fluorescence during amplification.

10. A method for monitoring the increase in double-stranded DNA during amplification of a target nucleic acid in a sample, wherein said method comprises the steps of:
   (a) providing a mixture that comprises all components necessary for the selective amplification of said target nucleic acid by polymerase chain reaction (PCR) containing said sample and a DNA binding agent, wherein said agent is characterized as providing a detectable signal when bound to double-stranded nucleic acid which signal is greater than the amount of said signal provided by said agent when it is unbound:
   (b) determining the amount of said signal produced by the mixture of step (a);
   (c) treating said mixture under conditions for amplifying said target nucleic acid; and (d) determining the amount of said signal produced by said mixture during said treating step (c).

11. The method of claim 10, wherein at steps (b) and (d), an optic fiber and spectra fluorometer are used to determine the amount of signal produced during said treating step.

12. The method of claim 11, wherein said DNA binding agent is an intercalating agent.

13. The method of claim 11, wherein at step (d) the amount of signal is determined continuously throughout the amplification reaction.

14. The method of claim 12, wherein said intercalating agent is a fluorescent dye.

15. The method of claim 14, wherein said fluorescent dye is ethidium bromide.

16. A kit for amplifying a target nucleic acid, that comprises a PCR buffer that comprises an intercalating age wherein said intercalating agent is characterized as providing a detectable signal when bound to double stranded DNA, which signal is greater than the signal provided by said intercalating agent when it is unbound and at least one pair of PCR amplification primers.

17. The kit of claim 16, wherein said intercalating agent is a fluorescent dye.

18. The kit of claim 17, wherein said fluorescent dye is ethidium bromide.

19. The kit of claim 18, wherein said ethidium bromide is present at a concentration suitable to provide between 0.15 $\mu$M and 40.6 $\mu$M dye in a PCR reaction.

20. The kit of claim 19, wherein said buffer also comprises Tris-HCl, pH 8.0–8.3 and KCl, each present in a concentration suitable for amplifying a target nucleic acid in a PCR.

21. The kit of claim 19 that also comprises a DNA polymerase, $MgCl_2$, and dNTPs.

\* \* \* \* \*